(12) United States Patent
Nishimura (10) Patent No.: US 8,562,604 B2
(45) Date of Patent: Oct. 22, 2013

(54) BIPOLAR HIGH FREQUENCY TREATMENT DEVICE

(76) Inventor: Miyuki Nishimura, Okaya (JP)

(*) Notice: Subject to any disclaimer, the term of this patent is extended or adjusted under 35 U.S.C. 154(b) by 1680 days.

(21) Appl. No.: 10/568,871

(22) PCT Filed: Aug. 19, 2004

(86) PCT No.: PCT/JP2004/011924
§ 371 (c)(1),
(2), (4) Date: Feb. 8, 2007

(87) PCT Pub. No.: WO2005/016163
PCT Pub. Date: Feb. 24, 2005

(65) Prior Publication Data
US 2007/0149971 A1    Jun. 28, 2007

(30) Foreign Application Priority Data
Aug. 19, 2003   (JP) ................... 2003-294810

(51) Int. Cl.
*A61B 18/14* (2006.01)
(52) U.S. Cl.
USPC ............................. 606/51; 606/52
(58) Field of Classification Search
USPC ......... 606/41, 51–52, 205–209; 600/562–564
See application file for complete search history.

(56) References Cited

U.S. PATENT DOCUMENTS

| | | | | |
|---|---|---|---|---|
| 4,669,471 A * | 6/1987 | Hayashi | ........................ | 606/205 |
| 5,151,102 A * | 9/1992 | Kamiyama et al. | .............. | 606/51 |
| 6,743,230 B2 * | 6/2004 | Lutze et al. | ...................... | 606/51 |
| 2001/0021860 A1 * | 9/2001 | Ouchi | ........................... | 606/205 |
| 2002/0013595 A1 | 1/2002 | Yamamoto | | |
| 2002/0123667 A1 * | 9/2002 | Ouchi | ........................... | 600/201 |
| 2003/0199869 A1 * | 10/2003 | Johnson et al. | ................. | 606/50 |
| 2004/0019352 A1 * | 1/2004 | Kidooka | ......................... | 606/48 |

FOREIGN PATENT DOCUMENTS

| | | |
|---|---|---|
| JP | 11-155875 A | 6/1999 |
| JP | 2000-271128 A | 10/2000 |
| JP | 2002-65598 | 3/2002 |
| JP | 2004-105499 A | 4/2004 |
| JP | 2004-113328 A | 4/2004 |
| WO | 2005/016163 | 2/2007 |

OTHER PUBLICATIONS

International Preliminary Report on Patentability dated Apr. 12, 2006 in PCT/JP2004/011924 (WO 2005/016163).
Notification of Reasons of Rejection dated Jun. 25, 2010 in Japanese Patent Appln No. 2005-513212.

* cited by examiner

*Primary Examiner* — Michael Peffley
*Assistant Examiner* — Samantha Good
(74) *Attorney, Agent, or Firm* — Browdy and Neimark, PLLC (57) ABSTRACT

Provided is a bipolar high frequency treatment device including a catheter tube insertable into a body through a treatment device passage of an endoscope; a first forceps blade and a second forceps blade at the top end of the catheter tube, which first forceps blade and second forceps blade can be opened and closed by operating from outside the body; a support member for supporting the first forceps blade and the second forceps blade so that the blades are able to open and close; and a voltage supplier for supplying a high frequency voltage to the first forceps blade and the second forceps blade, wherein the first forceps blade and the second forceps blade are electrically insulated with an insulating element.

18 Claims, 5 Drawing Sheets

BIPOLAR HIGH FREQUENCY TREATMENT DEVICE

BACKGROUND OF THE INVENTION

1. Technical Field

The present invention relates to a bipolar high frequency treatment device, which aims at improvement of insulation properties between a first forceps blade and a second forceps blade.

2. Background Art

As a conventional forceps type electric treatment device, for example, there is a device disclosed in Japanese Patent Application Laid-Open No. 11-155875 (Patent Document 1). This forceps type electric treatment device of Patent Document 1, according to the claims for the patent, is "a forceps type electric treatment device, comprising: a flexible catheter tube insertable into a body; a first forceps blade installed at the distal end side of the catheter tube and having a first cup-shaped concavity formed therein; a second forceps blade installed at the distal end side of the catheter tube and having a second cup-shaped concavity formed therein; a support device holding the first forceps blade and the second forceps blade so that they are able to move around a fulcrum shaft to open and close and that the first concavity and the second concavity come face to face; a first electrode formed in the first forceps blade; a second electrode formed in the second forceps blade; and voltage supply means connected to the proximal end side of the catheter tube so that high frequency voltage is supplied between the first electrode and the second electrode, wherein an intermediate insulating spacer is interposed between the first forceps blade and the second forceps blade that are held so that they are able to move around the fulcrum shaft to open and close" (see claim 1 of Patent Document 1). In a preferable mode for carrying out the invention, the device is a forceps type electric treatment device "wherein an insulating member is interposed between the fulcrum shaft and the first forceps blade and/or the second forceps blade" (see claim 2 of the Patent Document 1). In another preferable mode the device is a forceps type electric treatment device "wherein a sideward insulating spacer is interposed between the first forceps blade and/or the second forceps blade, which are held so that they are able to open and close around the fulcrum shaft, and the support device" (see claim 3 of Patent Document 1). In still another preferable mode the device is a forceps type electric treatment device "wherein a portion of the sideward insulating spacer protrudes from the outer periphery of the support device" (see claim 4 of Patent Document 1). In a further preferable mode, the device is a forceps type electric treatment device "wherein the sideward spacer has an elongated shape along the longitudinal direction of the support device" (see claim 5 of Patent Document 1).

Although there is no limitation imposed on the shape of the "intermediate spacer" in the claims of Patent Document 1, it is clear that the intermediate spacer is a disc-shaped flat plate in view of the whole specification.

Consequently, when the first forceps blade and the second forceps blade are in a closed state, the space between a first link rear end portion and a second link rear end portion, and the space between a first link and a second link become an insulating distance. The forceps type electric treatment device to be inserted into the body is has an insulating distance of approximately 0.5 mm since the diameter of the catheter tube insertable into the body is 2 to 3 mm. The high frequency current has a property of running through the surface of a conductive body. Consequently, if the insulating distance is approximately 0.5 mm, it is not sufficient for the purpose of insulating, and there is a possibility of causing the short-circuit or a leakage of the high frequency current.

Furthermore, in the forceps type electric treatment device of Patent Document 1, as shown in FIGS. 1 and 3 of Patent Document 1, since a pair of support elements in a bifurcated shape are formed at the top end portion of the support device, a pair of support elements are sometimes extremely opened or have torsion when the top end portion of the support device is processed. Then, in case the first forceps blade and the second forceps blade are attached to the top end portions of the pair of support elements, the attachment causes shaking or the first forceps blade and the second forceps blade are incapacitated to pivot smoothly because they are fastened too tight.

In the forceps type electric treatment device of Patent Document 1, as shown in FIG. 3 thereof, one conducting path is formed by the first forceps blade, the first link rear end portion, the first link element, a driving element and a conductive wire, and further, the other conducting path is formed by the second forceps blade, the second link rear end portion, a metallic washer, the support element, the support device and a coil tube. In the forceps type electric treatment device having a configuration according to Patent Document 1, when the first forceps blade and the second forceps blade are in an opened state, there is a possibility that the first forceps blade and the second link rear end portion are electrically contacted, and further, the second forceps blade and the first link rear end portion are electrically contacted. Consequently, for fear of such electrical contact, there arises an inconvenience that the first forceps blade and the second forceps blade cannot be opened to the fullest, and the first forceps blade and the second forceps blade cannot be widened so as to fit to the size of the lesion region existing in the body. Consequently, it has been practically impossible to open the first forceps blade and the second forceps blade so as not to contact each other inside the body.

[Patent Document 1] Japanese Patent Application Laid-Open No. 11-155875

The present invention has been made in order to solve the above-described problem, and an objective of the present invention is to provide a bipolar high frequency treatment device, which does not cause a leakage or short-circuit of the high frequency current and is safely operable when the first forceps blade and the second forceps blade are electrified.

Another objective of the present invention is to provide a bipolar high frequency treatment device, which does not generate a leakage or short-circuit of the high frequency current, can realize a smooth opening and closing of the first forceps blade and the second forceps blade, and can easily control the maximum opening state with the first forceps blade and the second forceps blade.

Still another objective of the present invention is to provide a bipolar high frequency treatment device, which, even when the high frequency current is allowed to flow while gripping the lesion region with the first forceps blade and the second forceps blade, the lesion region tissue can be prevented from adhering to the first forceps blade and/or the second forceps blade.

SUMMARY OF THE INVENTION

The bipolar high frequency treatment device according to the present invention comprises: a catheter tube insertable into a body through a treatment device passage of an endoscope; a first forceps blade and a second forceps blade at the top end of the catheter tube, which first forceps blade and second forceps blade can be opened and closed by operating from outside the body; a support member for supporting the first forceps blade and the second forceps blade so that the blades are able to open and close; and a voltage supplier for supplying a high frequency voltage to the first forceps blade and the second forceps blade, wherein the first forceps blade comprises a first grip portion, a first pivot support portion coupled with a wire transmitting an operating force from outside of the body, a first supported portion located midway between the first grip portion and the first pivot support portion and pivotably supported by the support member, and is made of an electrically conductive material;

wherein the second forceps blade comprises a second grip portion, a second pivot support portion coupled with a wire transmitting an operation force from outside the body, a second supported portion located midway between the second grip portion and the second pivot support portion and pivotably supported by the support member, and is made of an electrical conductive material; and wherein the support member is made of an insulating material, and comprises a separation element electrically separating the first pivot support portion and the second pivot support portion when the first grip portion and the second grip portion are closed so as to come face to face.

According to this configuration, by making the separation element completely separate the first pivot support portion from the second pivot support portion, the bipolar high frequency treatment device can be provided, which can safely operate without causing a leakage or short-circuit of the high frequency current between the first forceps blade and the second forceps blade.

In the bipolar high frequency treatment device according to the present invention, the first forceps blade has the first supported portion and the first pivot support portion formed in the shape of a continuous plate, and the first supported portion has a first grip portion formed at the end portion thereof, opposite the first pivot support portion, and the second forceps blade has the second supported portion and the second pivot support portion formed in the shape of a continuous plate, and the second supported portion has a second grip portion formed at the end portion thereof, opposite the second pivot support portion.

According to this configuration, the first supported portion and the first pivot support portion are formed in the shape of a continuous plate, and the second supported portion and the second pivot support portion are formed in the shape of a continuous plate, and the first grip portion and the first pivot support portion are integrally formed, and the second grip portion and the second pivot support portion are integrally formed, so that the first grip portion and the second grip portion can be closed so as to come face to face. Therefore, a safely operable bipolar high frequency treatment device can be provided, which is comprised by compactly fixing the first forceps blade and the second forceps blade into the support portion.

In the bipolar high frequency treatment device according to this invention, the first grip portion comprises a first storing portion with the shape of a concavity and a first connecting portion to connect the first storing portion with the first supported portion, and the first connecting portion is formed so as to broaden toward the first grip portion from the first supported portion, and the second grip portion comprises a second storing portion with the shape of a concavity and a second connecting portion to connect the second storing portion with the second supported portion, and the second storing portion is formed so as to broaden toward the second grip portion from the second supported portion.

According to this configuration, the first grip portion comprises the first storing portion and the first connecting portion, and the second grip portion comprises the second storing portion and the second connecting portion, and the first connecting portion and the second connecting portion are formed so as to broaden toward the end, respectively. Therefore, when the first forceps blade and the second forceps blade are opened, the first pivot support portion in the shape of a plate does not contact the second storing portion, and the second pivot support portion in the shape of a plate does not contact the first storing portion, which results in a safely operable bipolar high frequency treatment device.

In the bipolar high frequency treatment device according to the present invention, the support member comprises:

a tube receiving portion formed in the shape of a cylinder, into which the catheter tube is fitted, a pair of side portions separated and extended in the direction opposite the receiving space of the catheter tube in the tube receiving portion; and a separation element having a first receiving groove for receiving the first pivot support portion, a second receiving groove for receiving the second pivot support portion, and a central element for separating the first receiving groove and the second receiving groove.

According to this configuration, the separation element provided at the ends of the side portions, which side portions extend from one end of the tube receiving portion and are formed in parallel with each other, is formed so as to have the central element separating the first receiving groove for receiving the first pivot support portion and the second receiving groove for receiving the second pivot support portion. Therefore, the pivoting movements of the first pivot support portion and the second pivot support portion in the first receiving groove and the second receiving groove are smoothly performed without becoming shaky. Moreover, there is neither a leakage nor short-circuit of the high frequency current between the first pivot support portion and the second pivot support portion separated by the central element, which results in a safely operable bipolar high frequency treatment device.

In the bipolar high frequency treatment device according to this invention, the first receiving groove comprises a first opening-degree control portion to control an opening angle of the first forceps blade when the first forceps blade and the second forceps blade are opened, and the second receiving groove comprises a second opening-degree control portion to control an opening angle of the second forceps blade when the first forceps blade and the second forceps blade are opened.

According to this configuration, since the first receiving groove is provided with the first opening-degree control portion and the second receiving groove is provided with the second opening-degree control portion, respectively, the first grip portion and the second grip portion are opened widely to such an extent that the first grip portion contacts the second pivot support portion and the second grip portion contacts the first pivot support portion, in such an manner that there is neither a leakage nor short-circuit of the high frequency current between the first grip portion and the second grip portion, which leads to a safely operable bipolar high frequency treatment device.

In the bipolar high frequency treatment device according to this invention, the support member integrally has the tube receiving portion, the side portions, and the separation element.

According to this configuration, since the whole support member is integrally formed, the strength of the whole support member can be increased.

In the bipolar high frequency treatment device according to this invention, each of the opposite surfaces of the first grip portion and the second grip portion is made of ceramic.

According to this configuration, since each of the mutually opposite surfaces of the first forceps blade and the second forceps blade is made of ceramic, when the high frequency current is allowed to flow to the first forceps blade and the second forceps blade made of electrical conductive materials so as to cauterize an organism tissue, a safely operable bipolar high frequency treatment device can be provided without any organism tissue adhering or fixed to the opposite surfaces.

In the bipolar high frequency treatment device according to this invention, the catheter tube has at least two through holes running from the top end thereof located at the side of the support member, to the rear end, and has a notch at the support-member-side end of the catheter tube, into which notch a part of an protruding portion formed in the separation element can be inserted.

According to this configuration, the catheter tube has at least two through holes penetrating from its top end toward the rear end, and a wire allowing the high frequency current to flow is inserted into each of the through holes. Since a portion of the separation element is inserted into the notched portion formed in the top end of the catheter tube, the wire running through one of the through holes and coming out of the top end of the catheter tube can be separated and made independent from the wire running through the other through hole and coming out of the top end. Therefore, the wires do not contact each other. Consequently, there is neither a leakage nor short-circuit of the high frequency current between the wires, and a safely operable bipolar high frequency treatment device can be provided.

In the bipolar high frequency treatment device according to this invention, the catheter tube has one through hole running from the support-member-side end to the rear end, and an insulating separation member is placed in the vicinity of the top end of the catheter tube, which is inserted into the support member, by penetrating the support member and the catheter tube in the direction of the diameter of this catheter tube.

According to this configuration, since the insulating separation member penetrates the catheter tube in the direction of the diameter thereof inside the catheter tube in the vicinity of the top end of the catheter tube having one through hole running from the top end to the rear end, the two wires allowing the high frequency current to flow can be separated, and the support member and the catheter tube can be firmly and reliably fixed by mechanical connection. Therefore, there is neither a leakage nor short-circuit of the high frequency current between the wires, and without disconnection of the catheter tube and the support member, a safely operable bipolar high frequency treatment device can be provided.

BEST MODE FOR CARRYING OUT THE INVENTION

I am going to describe the best mode for carrying out the invention below, referring to the attached drawings, in order to describe the present invention more in detail.

First Embodiment

Figure 1:
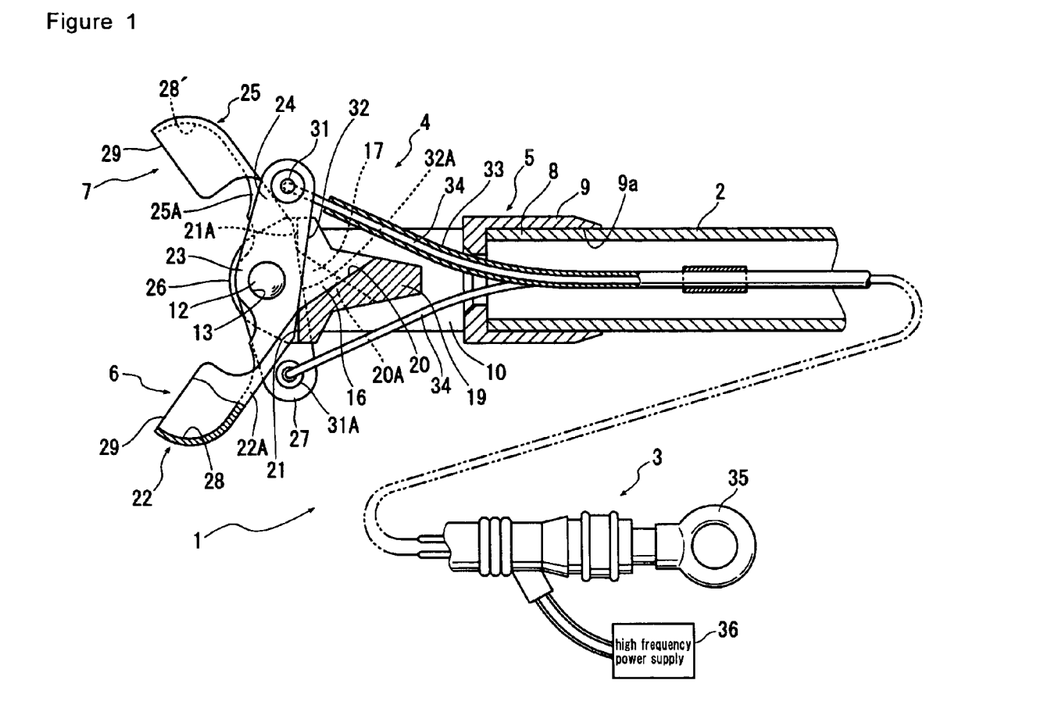
FIG. 1 is a partially notched longitudinal cross sectional view showing a bipolar high frequency treatment device according to the first embodiment of the present invention.

As shown in FIG. 1, a bipolar high frequency treatment device 1 according to the first embodiment of the present invention comprises a catheter tube 2, which is, for example, which can be inserted into a stomach and a large intestine in the body through a treatment device passage in an endoscope (not shown). This catheter tube 2 is made of a soft insulating material having flexibility. For the insulating material, for example, synthetic resins and the like, such as polyethylene, polypropylene, polyacetal, polyester, polyether sulfone, polyether ether ketone (PEEK), polyimide, fluorine-containing resins and the like can be cited. A material having suitable elasticity is selected depending on the purpose.

While the catheter tube 2, if having a diameter size insertable into the body, has no limitation on its diameter size, usually, the outer diameter is 2 to 3 mm, and the inner diameter is 0.5 to 2.5 mm, into which catheter wires to be described later can be inserted. The catheter tube 2 with the diameter sizes makes it possible to smoothly insert the bipolar high frequency treatment device 1 into the body through the treatment device passage in the endoscope.

Furthermore, the catheter tube 2 is provided with an operating portion 3 at the rear end thereof, and a working portion 4 at the top end thereof. In the present invention, since the top end of the catheter tube 2 provided with the working portion 4 is located faraway from the operating portion 3, it is sometimes referred to as a distal end. The working portion 4 has a configuration, comprising a support member 5, a first forceps blade 6 and a second forceps blade 7.

Figure 2:
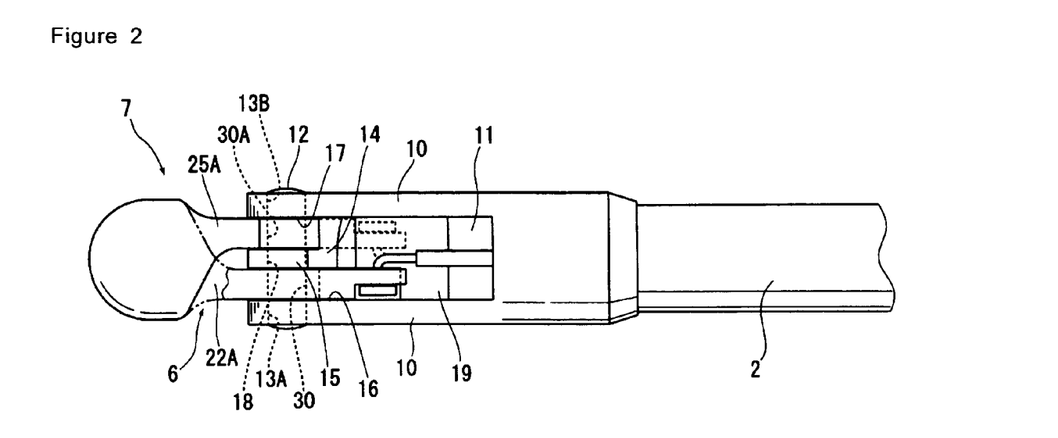
FIG. 2 is a top plan view of the bipolar high frequency treatment device shown in FIG. 1.

The support member 5 is cylindrical, in particular, in the shape of a general circular cylindrical body, and comprises: a tube receiving portion 9 having an opening portion 9a at one end thereof into which the top end, or the distal end 8 of the catheter tube 2 can be inserted; a pair of side portions 10 extending from the tube receiving portion 9 in the direction opposite the opening portion 9a and formed to be parallel with each other, as shown in FIGS. 1 and 2; and a separation element 14 placed at the top or distal end side of the side portions 10 and formed so as to connect the side portions 10 with each other. The support member 5 is designed to have all these elements in one united body. The support member 5 has a cavity 11 surrounded by the pair of side portions 10, the tube receiving portion 9, and the separation element 14. The top or distal end portion of one of the side portions 10 has a first through hole 13A bored to receive a pin 12 to be inserted, and the top end portion of the other side portion 10 is has a second through hole 13B bored coaxially with the first through hole 13A to receive the pin 12 to be inserted.

The separation element 14, as shown in FIG. 1, comprises: a central element 15 located at the top or distal end portion opposite the tube receiving portion 9 of the support member 5; a first receiving groove 16 formed by the central element 15 and the pair of side portions 10, into which first receiving groove 16 a first pivot support portion 24 of the first forceps blade 6 can be inserted; and a second receiving groove 17 formed by the central element 15 and the other side portion 10, into which second receiving groove 14 a second pivot support portion 27 of the second forceps blade 7 can be inserted in a manner electrically separated from the first forceps blade 6. The first receiving groove 16 and the second receiving groove 17 are in the relationship of rotation symmetry of 180 degrees around the central axis of the support member 5. Furthermore, in the separation element 14, the central element 15 has a third through hole 18 corresponding to the first through hole 13A formed in the side portion 10 and the second through hole 13B formed in the other side portion 10. The first through hole 13A, the second through hole 13B, and the third through hole 18 are formed so as to be aligned with the common central line.

A protruding portion 19 extending toward the cavity 11 is formed on the separation element 14. The upper face of the protruding portion 19 is formed so as to become inclined toward the central axis of the support member 5, and the lower face of the protruding portion 19 is formed so as to become inclined toward the central axis of the support member 5. The upper face and the lower face of the protruding portion 19 are in a positional relationship of rotation symmetry of 180 degrees around the central axis of the support member 5.

The first receiving groove 16 of the separation element 14, as shown in FIG. 1, is provided with a first inclined bottom 20 adjoining the inclined face of the protruding portion 19, and a first opening-degree control bottom 21 continuing to the first inclined bottom 20 and extending in a direction going away from the central axis of the support member 5. This first opening-degree control bottom 21 is one example of the first opening control portion in the present invention. Similarly, the second receiving groove 17 in the separation element 14, as shown in FIG. 1, is provided with a second inclined bottom 20A adjoining the inclined face of the protruding portion 19, and a second opening-degree control bottom 21A continuing to this second inclined bottom 20A and extending in a direction going away from the central axis of the support member 5. This second opening-degree control bottom 21A is also one example of the second opening control portion in the present invention. The first inclined bottom 20 and the second inclined bottom 20A are in the relationship of rotation symmetry of 180 degrees around the central axis line of the support member 5, and the first opening-degree control bottom 21 and the second opening-degree control bottom 21A are also in the same relationship.

Thus, the separation element 14 bridges the pair of side portions 10, 10. Moreover, since the pair of side portions 10, 10 and the separation element 14 are formed in one united body, the strength of the support member 5 is increased.

In general, materials for the support member 5 and the pin 12 are not limited, as long as the materials have electrical insulating properties. For example, the main body of the support member may be made of a metallic material such as stainless steel, carbon steel, gold, silver, platinum, aluminum, or the like, and all the surface of the main body is covered with an insulating film. The insulating film is preferably made of a plastic that is great in mechanical strength and excellent in toughness, such as PEEK (polyether ether ketone), PPS (polyphenylene sulfide), polyimide resin and the like, or a ceramic material such as zirconia and the like. The support member 5 can be molded easily from these plastic and ceramic materials, and the support member 5 can be manufactured at a low price. Furthermore, as described above, this support member 5, the pair of side portions 10 and 10, the tube receiving portion 9, and the separation element 14 are integrally formed. In this manner, when the whole support member 5 is formed in one united body, the strength of the whole support member 5 can be increased.

The first forceps blade 6, as shown also in FIG. 1, comprises a first grip portion 22, a first supported portion 23, and the first pivot support portion 24, and these portions are formed in one united body. The second forceps blade 7, as shown in FIG. 1, also comprises a second grip portion 25, a second supported portion 26, and the second pivot support portion 27, and these portions are formed in one united body.

Each of the first grip portion 22 and the second grip portion 25 comprises first storing portions 28 and 28', respectively, and the end faces of the first storing portions 28, 28' respectively have contacting faces 29 which contact each other when the first grip portion 22 and the second grip portion 25 are superposed. This contacting face 29 is also referred to as a joining surface.

Furthermore, the first grip portion 22 comprises the first storing portion 28 in the shape of a concavity and a first connecting portion 22A which has a tapering shape and connects this first storing portion 28 with the first supported portion 23. The first connecting portion 22A becomes a broadened shape, when viewed from the location where the first supported portion 23 is placed. The second grip portion 25 is also continued from the second storing portion 28', and is continued to the second supported portion 26, while having a shape becoming narrower toward the second supported portion. The region tapering toward the second supported portion 26, that is, the region becoming broadened toward the second storing portion 28', when seen in reverse, is the second connecting portion 25A.

The first supported portion 23 fits into the first receiving groove 16, and comprises a plate-like portion with an insertion hole 30 to receive the pin 12 to be inserted, and broadens toward the first storing portion 28 from one end of this plate-like portion, and finally to the first grip portion 22. This region broadened toward the first storing portion is the first connecting portion 22A. The other end of the first support portion 23 is extended up to the first pivot support portion 24. The second supported portion 26 has the same configuration as the first supported portion 23. Reference numeral 25A denotes the second connecting portion.

The first pivot support portion 24 comprises a plate-like portion with a plate-like shape similar to the shape of the first supported portion 23, which plate-like portion continues to the first supported portion 23. The plate-like portion has an attachment hole 31 in the vicinity of the top end thereof. The first pivot support portion 24 has a linear contact edge portion 32 formed continuously from the outside surface of the first storing portion 28, at the lower end of the plate-like portion. The contact edge portion 32 fits the first forceps blade 6 into the first receiving groove 16, and in more detail, fits the first supported portion 23 and the first pivot support portion 24 into the first receiving groove 16. When the pin 12 is inserted into the insertion hole 30 and thus the first forceps blade 6 is pivotably accommodated in the first receiving groove 16, the contact edge portion 32 is accommodated in the first receiving groove 16 so as to face the first inclined bottom 20 of the first receiving groove 16 with a little space in between (see FIG. 3). In the state in which the first supported portion 23 and the first pivot support portion 24 are accommodated in the first receiving groove 16 and the second supported portion 26 and the second pivot support portion 27 are accommodated in the second receiving groove 17, the contacting face 29 of the first grip portion 22 and that of the second grip portion 25 are in a contacted state, that is, in a joined state. In other words, the first forceps blade 6 and the second forceps blade 7 are in a closed state.

Furthermore, as shown in FIG. 1, the contact edge portion 32 abuts against the first opening-degree control bottom 21, so that the contact edge portion 32 of the first forceps blade 6, in the state (see FIG. 3) in which the contact edge portion 32 faces the first inclined bottom 20 with being slightly away from it, pivots in a direction to separate from the first inclined bottom 20, or in a direction to open the first forceps blade 6 and the second forceps blade 7. Then, the pivoting of the first forceps blade 6 is controlled so that the angle between the first forceps blade 6 and the second forceps blade 7 does not exceed a predetermined angle.

The second forceps blade 7 also comprises a contact edge portion 32A and an attachment hole 30A having the same configuration as that of the first forceps blade 6. Since the contact edge portion 32A and the attachment hole 30A have the same configuration as that of the first forceps blade 6, the detailed description thereof is omitted.

The angle of the inclination of the first inclined bottom 20 of the first receiving groove 16, that is, the angle between the virtual plane which includes the ridgeline formed by the inclined face of the first inclined bottom 20 and the first opening-degree control bottom 21, and is parallel with the central axis of the support member 5, and the first inclined bottom 20 of the first receiving groove 16 should suitably be designed as well as the angle of the inclination of the second inclined bottom 20A of the second receiving groove 17, so that the contacting face 29 of the first grip portion 22 and that of the second grip portion 25 are joined when the contact edge portion 32 of the first pivot support portion 24 faces the first inclined bottom 20 with a little space in between (see FIG. 3) and the contact edge portion 32A of the second pivot support portion 27 faces the second inclined bottom 20A of the second receiving groove 17 with a little in between. This design will, when the first grip portion 22 and the second grip portion 25 are superposed, provide no gap between the contacting faces 29.

Furthermore, the angle of the inclination of the second opening-degree control bottom 21A, which is one example of the second opening-degree control portion, that is, the angle between the virtual plane which includes the ridgeline formed by the inclined face of the second inclined bottom 20A and the second opening-degree control bottom 21A, and is parallel with the central axis of the support member 5, and the second opening-degree control bottom 21A should suitably be designed, so that the second pivot support portion 27 does not contact the first grip portion 22 and similarly the first pivot support portion 24 does not contact the second grip portion 25 when the first forceps blade 6 and the second forceps blade 7 are put into an opened state. If the angle is designed in this manner, for example, the first grip portion 22 and the second pivot support portion 27 do not contact each other, and no inconvenience, such as a damage to the members, a leakage of the high frequency current and the like, is caused.

The first opening-degree control bottom 21 and the second opening-degree control bottom 21A control the angle between the first grip portion 22 and the second grip portion 25. Consequently, the location of the first opening-degree control bottom 21 decided depending on the angle of opening between the first grip portion 22 and the second grip portion 25.

The first and second forceps blades 6 and 7 are respectively made of a metal such as stainless steel and the like. The entire surfaces other than the contacting faces 29 may be covered with an insulating coating layer, for example, a ceramic coating layer. Furthermore, the entire parts other than the contacting faces 29 of the first forceps blade 6 and the second forceps blade 7 may be made of an insulating material, for example, ceramic such as $SiO_2$ and DLC (diamond-shaped carbon), or plastic such as polytetrafluoroethylene and the like, and the contacting faces 29 alone may be made of a conductive material, for example, such as metal. The whole surfaces of the first forceps blade 6 and the second forceps blade 7 may be coated with the above described insulating material, depending on the circumstances.

The capacity of the first storing portion 28 of the first grip portion 22 and that of the first storing portion 28' of the second grip portion 25 are not particularly limited, and they may suitably be decided according to the volume and the like of the biological tissue to be taken, for example, such as polyp and the like.

One end of a wire 34 with an insulating film 33 on the surface thereof is joined to the attachment hole 31 of the first forceps blade 6, and one end of the same or a similar wire 34 is joined to the attachment hole 31A of the second forceps blade 7, respectively. These wires 34 are extended and disposed in the catheter tube 2, and the other ends thereof are joined to the operating portion 3. The wires 34, 34 are made of a conductive material, for example, extremely thin wires or twisted wires formed from stainless steel wires. The wire 34 may, alternatively, have a structure with a core wire made of a conductive material, such as stainless steel, inserted into an insulating tube.

The operating portion 3 comprises a handle 35, and is structures so that the wires 34, 34 are pulled by pulling this handle 35.

In FIG. 1, reference numeral 36 denotes a high frequency power supply, and the high frequency current outputted from this high frequency power supply 36 is allowed to flow through the wires 34 and 34. Reference numeral 37 denotes a fixing device to fix the pair of wires 34 to each other in the catheter tube 2.

Next, the assembly of the bipolar high frequency treatment device 1 thus configured will be described.

First, the first supported portion 23 and the first pivot support portion 24 of the first forceps blade 6 are placed and accommodated in the first receiving groove 16. Similarly, the second supported portion 26 and the second pivot support portion 27 of the second forceps blade 7 are placed and accommodated in the second receiving groove 17. At this time, in the first receiving groove 16, the first supported portion 23 and the first pivot support portion 24, both of which have a plate-like shape, are nipped between the side surface of the central element 15 and the side surface of the side portion 10 so as not to be in a shaky state, and in the second receiving groove 17, the second supported portion 26 and the second pivot support portion 27, both of which have a plate-like shape, are nipped between the side surface of the central element 15 and the side surface of the side portion 10 so as not to be in a shake state.

The respective axial lines of the first through hole 13A formed in the side portion 10 of the support member 5, the insertion hole 30 formed in the first supported portion 23 provided of the first forceps blade 6, the third through hole 18 formed in the central element 15, the attachment hole 30A formed in the second supported portion 26 of the second forceps blade 7, and the second through hole 13B formed in the other side portion 10 of the support member 5 are aligned, and one pin, or the pin 12, is inserted into the first through hole 13A, the insertion hole 30, the third through hole 18, the attachment hole 30A and the second through hole 13B and fixed. Then, each of the first forceps blade 6 and the second forceps blade 7 can smoothly pivot in the first receiving groove 16 and the second receiving groove 17 around the pin 12.

Next, the operation of the treatment device will be described.

Figure 3:
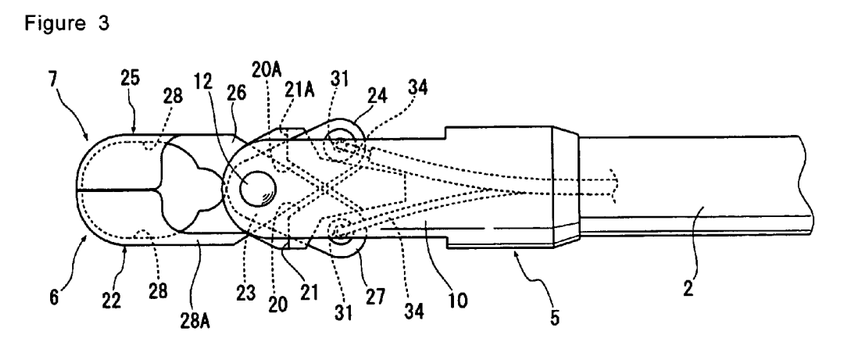
FIG. 3 is a side view of the bipolar high frequency treatment device shown in FIG. 2.

As shown in FIG. 3, the bipolar high frequency treatment device 1, in the state where the contacting face 29 of the first forceps blade 6 and that of the second forceps blade 7 contact each other and the first forceps blade 6 and the second forceps blade 7 are into the closed state, is sent to an affected area through the treatment device passage of, for example, an endoscope, with the first forceps blade 6 and the second forceps blade 7 taking the lead.

Here, as described above, to put the first forceps blade 6 and the second forceps blade 7 into a closed state, the user pulls the handle 35 of the operating portion 3, so that the pulling force on the handle 35 is transmitted to and exerted on the first pivot support portion 24 and the second pivot support portion 27 through the wires 34, 34.

Then, when the first pivot support portion 24 and the second pivot support portion 27 are in an opened state, as shown in FIG. 1, around the pin 12, the first pivot support portion 24 moves toward the first inclined bottom 20 of the first receiving groove 16, and the second pivot support portion 27 also moves toward the second inclined bottom 20A of the second receiving groove 17. These movements, when the first forceps blade 6 and the second forceps blade 7 are put into the closed state, make the respective contact edge portions 32 of the first pivot support portion 24 and the second pivot support portion 27 face the first inclined bottom 20 and the second inclined bottom 20A with being slightly away from them. In this state, even if the handle 35 is pulled more, since the first forceps blade 6 and the second forceps blade 7 are in the closed state, the first pivot support portion 24 and the second pivot support portion 27 are no longer able to pivot around the pin 12. In this manner, while the bipolar high frequency treatment device 1 is in the body, with the first forceps blade 6 and the second forceps blade 7 being in the closed state, the operating portion 3 is kept outside the body.

The first forceps blade 6 and the second forceps blade 7 in the body can be opened in the following manner.

First, when the handle 35 is pushed, the pushing pressure is transmitted to the first pivot support portion 24 and the second pivot support portion 27 through the wire 34. Upon the receipt of the pushing pressure, the first pivot support portion 24 pivots around the pin 12 so as to leave the first inclined bottom 20 of the first receiving groove 16. The first pivot support portion 24, which continues receiving the pushing pressure, still continues pivoting. When the contact edge portion 32 of the first pivot support portion 24 abuts against the first opening-degree control bottom 21, the first pivot support portion 24 cannot pivot any more.

On the other hand, when the pushing pressure is transmitted to the second pivot support portion 27, by the operation of the first pivot support portion 24, the second pivot support portion 27 also works, and eventually, the pivoting of the second pivot support portion 27 is stopped by the second opening control bottom 21A.

In the illustrated example, since the opening and closing operations of the first forceps blade 6 and the second forceps blade 7 are performed by both operations of pulling and pushing of the wires 34 without employing a link mechanism, a mechanical configuration to realize the opening and closing operations is extremely simple. This leads to a reduction of the causes of trouble, and consequently, the present invention can provide a bipolar high frequency treatment device capable of reliable operations.

As a result, the first pivot support portion 24 and the second pivot support portion 27 are put into an opened state as shown in FIG. 1.

Figure 4:
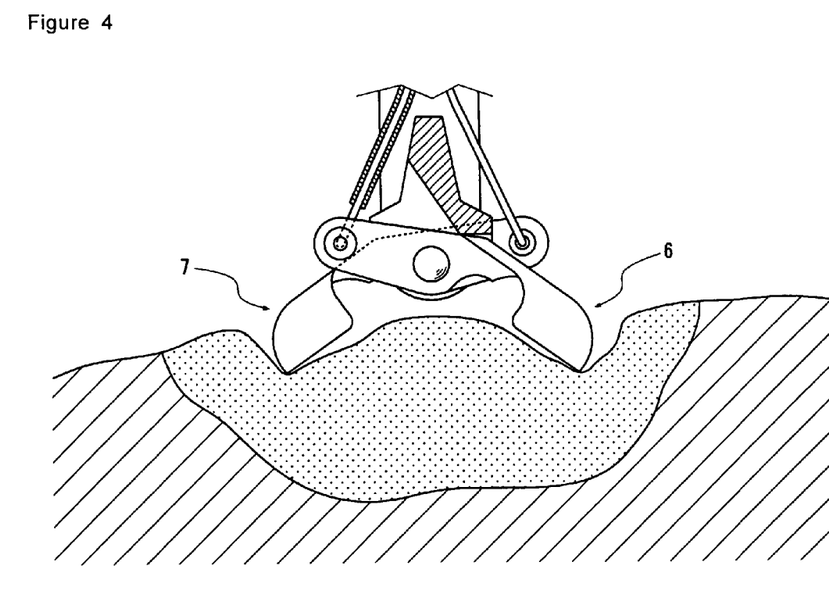
FIG. 4 is an explanatory drawing showing a state where the bipolar high frequency treatment device according to the first embodiment of the present invention is used.

In a case where a large affected area is treated with the bipolar high frequency treatment device 1, for example, when hemorrhage in a large area of the affected mucous membrane surface is coagulated and stopped with the bipolar high frequency treatment device 1, the first forceps blade 6 and the second forceps blade 7, both of which are kept open to the fullest extent, as shown in FIG. 1, are pushed onto an affected area 40, as shown in FIG. 4. Then, by operating the operating portion 3, a high frequency voltage from the high frequency power supply 36 is applied to the first forceps blade 6 and the second forceps blade 7 through the wires 34. Then, an affected area tissue contacting the first forceps blade 6 and the second forceps blade 7 is heated, the heating coagulates the tissue, and eventually, an arrest of hemorrhage is realized.

When the high frequency current is applied, a leakage or short-circuit of the high frequency current between the first forceps blade 6 and the second forceps blade 7 is prevented. This is because the first forceps blade 6 and the second forceps blade 7 are electrically separated by the separation element 14.

In more detail, as shown in FIG. 4, when the first forceps blade 6 and the second forceps blade 7 are in a state where both are kept open to the fullest extent, since the first supported portion 23 of the first forceps blade 6 and the second supported portion 26 of the second forceps blade 7 are electrically and distantly separated by the separation element 14, generation of the leakage or the electrical short circuit between the first supported portion 23 and the second supported portion 26 is prevented.

In the state in which the first forceps blade 6 and the second forceps blade 7 are kept open to the fullest extent, since the first pivot support portion 24 and the second pivot support portion 27 are separated from each other, this positional relationship causes neither a leakage nor electrical short-circuit caused between the first pivot support portion 24 and the second pivot support portion 27.

Since the first connecting portion 22A is formed in the first forceps blade 6 and the second connecting portion 25A is formed in the second forceps blade 7, even if the first forceps blade 6 and the second forceps blade 7 are widely opened, no contact is made between the first storing portion 28 of the first forceps blade 6 and the second pivot support portion 27 of the second forceps blade 7. Also, no electrical contact is made between the second storing portion 28' of the second forceps blade 7 and the first pivot support portion 24 of the first forceps blade 6. Consequently, electrical leakage or the electrical short-circuit caused by the contact of these portions can be prevented.

Since the first opening-degree control bottom 21 and the second opening-degree control bottom 21A are provided, the first forceps blade 6 and the second forceps blade 7 are not opened too much to lead to mutual contact, and this structure can also prevent the electrical leakage or the electrical short-circuit. The inclination angles of the first opening-degree control bottom 21 and the second opening-degree control bottom 21A can be adjusted by cutting and the like. The fact that the angle of the inclination is adjustable means that the bipolar high frequency treatment device according to the present invention is capable of adjusting the angles of opening of the first forceps blade 6 and the second forceps blade 7 according to the condition of the affected area, and in this point, it is a convenient device. By adjusting the locations of the first opening-degree control bottom 21 and the second opening-degree control bottom 21A backward and forward in the axial direction, the angles of opening of the first forceps blade 6 and the second forceps blade 7 can be set also to desired angles. For example, when it is considered that the angles of opening of the first forceps blade 6 and the second forceps blade 7 are not sufficient, the angles of opening can be easily changed to larger angles of opening by cutting the first opening-degree control bottom 21 and the second opening-degree control bottom 21A so that the locations of the first opening-degree control bottom 21 and the second opening-degree control bottom 21A are moved backward in the axial direction.

Figure 5:
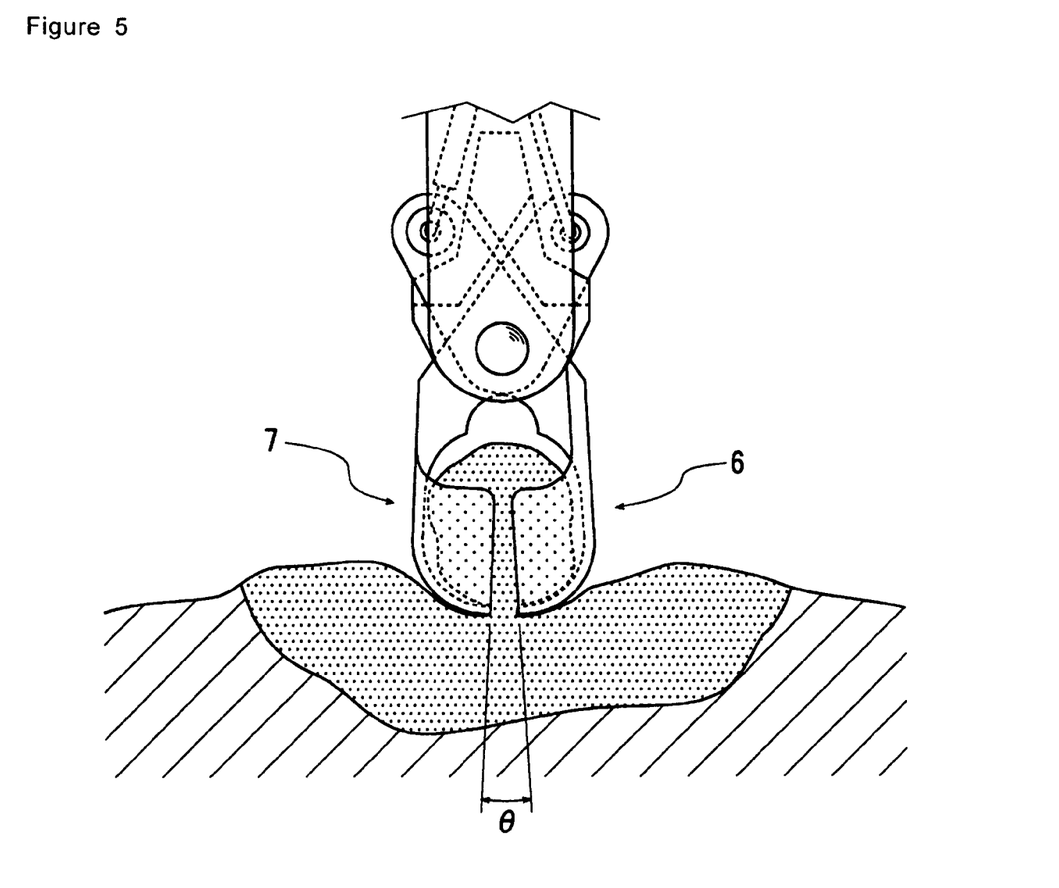
FIG. 5 is an explanatory drawing showing another state where the bipolar high frequency treatment device according to the first embodiment of the present invention is used.

When a protruding portion of the area to be treated, for example, a polyp is subjected to ablation, this bipolar high frequency treatment device is operated as follows. The polyp is nipped between the first forceps blade 6 and the second forceps blade 7, both of which are kept in an opened state toward the polyp. That is, a pulling force generated by pulling the handle 35 is transmitted to the first pivot support portion 24 and the second pivot support portion 27 through the wires 34. Upon the receipt of the pulling force, the first pivot support portion 24 and the second pivot support portion 27 pivot around the pin 12. Along with the pivoting of the first pivot support portion 24 and the second pivot support portion 27, the first grip portion 22 and the second grip portion 25 pivot around the pin 12 so as to mutually come closer. By this pivoting, the polyp is accommodated in the first storing portion 28 of the first grip portion 22 and the second storing portion 28' of the second grip portion 25, so that, as shown in FIG. 5, a state of gripping the polyp by the first grip portion 22 and the second grip portion 25 is realized.

Subsequently, by turning on a switch (not shown) of the high frequency power supply 36, the high frequency current is allowed to flow through the wires 34. When the high frequency current is allowed to flow to the first grip portion 22 and the second grip portion 25 through the wires 34, the current flows to the base of a tissue fragment nipped between the contacting face 29 of the first grip portion 22 and the contacting face 29 of the second grip portion 25, and the base of the tissue fragment is heated. As the current flow of the high frequency current is continued, eventually the tissue nipped between the contacting faces 29 is burnt off. The cut out polyp is confined to the internal space formed by the first storing portion 28 of the first grip portion 22 and the concave portion of the second grip portion 25.

On the other hand, while the high frequency current is allowed to flow through the first grip portion 22 and the second grip portion 25, the first supported portion 23 and the first pivot support portion 24 are being fitted into the first receiving groove 16, and the second supported portion 26 and the second pivot support portion 27 are being fitted into the second receiving groove 17. Therefore, the central element 15 makes the first supported portion 23 and the first pivot support portion 24 as well as the second supported portion 26 and the second pivot support portion 27 in an electrically insulated state. Consequently, there is no fear of causing the leakage and the like when the high frequency current is allowed to flow. In the present invention, the reason that the accident such as the leakage and the like does not occur while the high frequency current is being applied is that the first supported portion 23 and the first pivot support portion 24 as well as the second supported portion 26 and the second pivot support portion 27 are separated from each other by the central element 15. Consequently, in order to prevent a leakage of the high frequency current more reliably, the depth of the first receiving groove 16 is preferably designed so that large portions of the first supported portion 23 and the first pivot support portion 24 can be accommodated in the first receiving groove 16. With respect to the second receiving groove 17, it is also preferable that the depth thereof is designed similarly to that of the first storing grove 16.

A detailed description of the first embodiment according to the present invention has been made so far. However, the invention is not limited to the first embodiment but can be suitably modified and carried out within the scope of the invention, not apart from the spirit thereof.

Although the bipolar high frequency treatment device according to the present invention may be designed so that the contacting faces 29 of the first forceps blade 6 and the second forceps blade 7 are joined without space in between, depending on the circumstances, for example, as shown in FIG. 5, the contacting faces may be inclined with each other so that the contacting face 29 of the first forceps blade 6 and the contacting face 29 of the second forceps blade 7 are placed at an angle θ when the first forceps blade 6 and the second forceps blade 7 are closed. This embodiment makes it easier to grip a piece of tissue with the first forceps blade 6 and the second forceps blade 7 and burn it out.

Second Embodiment

Figure 6:
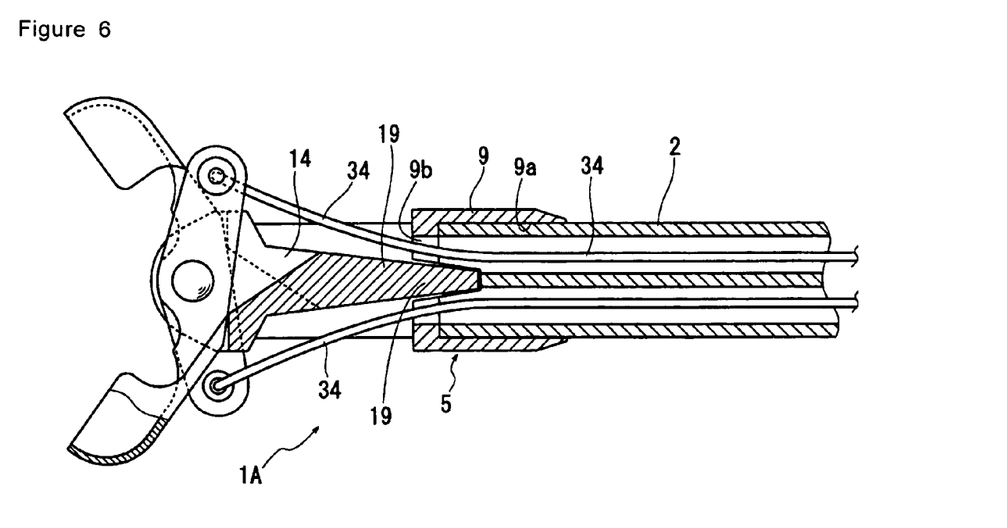
FIG. 6 is a cross sectional view showing the main parts of the bipolar high frequency treatment device according to the second embodiment of the present invention.
Figure 7:
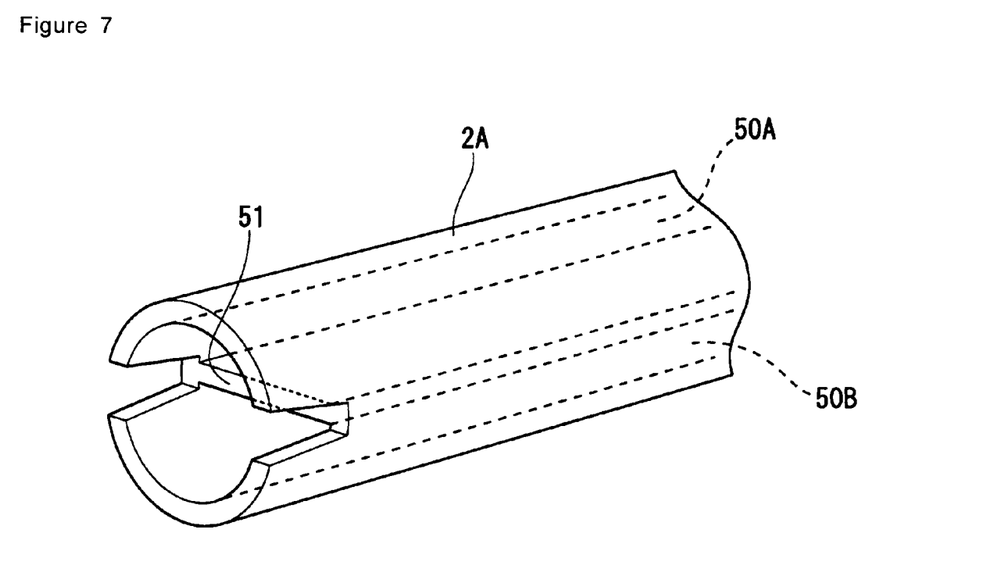
FIG. 7 is a perspective view showing the catheter tube shown in FIG. 6.

FIG. 6 is a cross sectional view showing the main parts of a bipolar high frequency treatment device according to the second embodiment of the present invention, and FIG. 7 is a perspective view showing a catheter tube shown in FIG. 6.

In this second embodiment, as shown in FIG. 6, the bipolar high frequency treatment device comprises a support member having a protruding portion 19 made by extending the top end portion of the separation element to an extent insertable to an opening 9b opposite the opening 9a of the tube receiving portion 9; and a catheter tube 2A having at least two through holes 50A and 50B passing from the top end to the rear end of the tube 2A and having a notch 51 capable of receiving the protruding portion 19 to be inserted into the top end, as shown in FIGS. 6 and 7. In this second embodiment, the tube comprising more than two through holes can be acquired as a multi lumen tube.

In a bipolar high frequency treatment device 1A shown in FIG. 6 as an example, the wire 34 is inserted into each of the through holes 50A and 50B in the catheter tube 2A. The wire 34 pulled out from the through hole 50A and the wire 34 pulled out from the through hole 50B are separated by the separation element 14, and extended to different locations.

In the bipolar high frequency treatment device 1A shown in FIG. 6, since the wires 34 and 34 are separated in the catheter tube 2A, never occurs the leakage or the electrical short-circuit caused by an electrical contact of the wires 34, 34 in the catheter tube 2A. Since the wires 34, 34 pulled out of the catheter tube 2A are separated by the separation element 14, never happens the leakage or the electrical short-circuit caused by the contact of the wires. Consequently, the bipolar high frequency treatment device comprising a catheter tube with at least two through holes running from the top, or support-member-side end to the rear end, and with a notch capable of receiving a portion of the separation element to be inserted into the top, or support-member-side of the catheter tube, has neither the leakage nor the electrical short-circuit and can be safely operated.

Although the notch 51 is V-shaped in FIG. 6, there is no particular limitation on the shape thereof as far as it is shaped so that one end of the separation element 14 can be inserted into it, depending on the shape of the end of the separation element 14.

Third Embodiment

Figure 8:
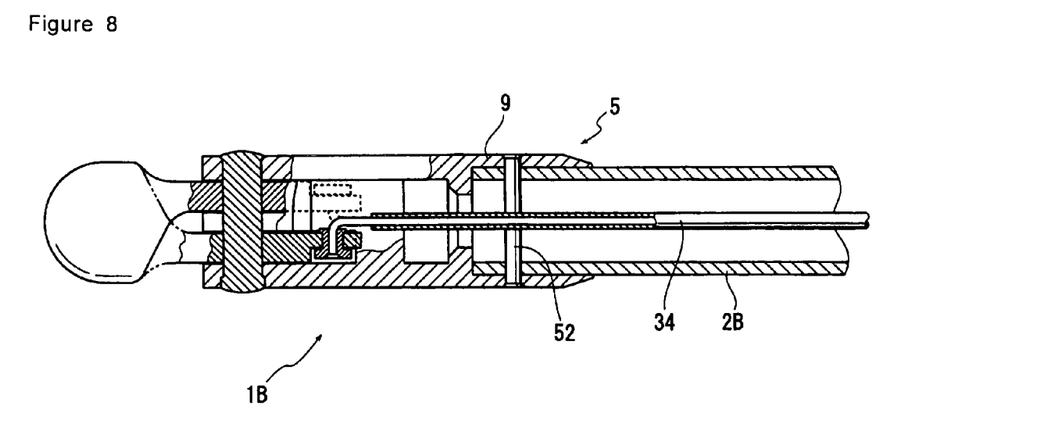
FIG. 8 is a horizontal cross sectional view showing the main parts of the bipolar high frequency treatment device according to the third embodiment of the present invention.
Figure 9:
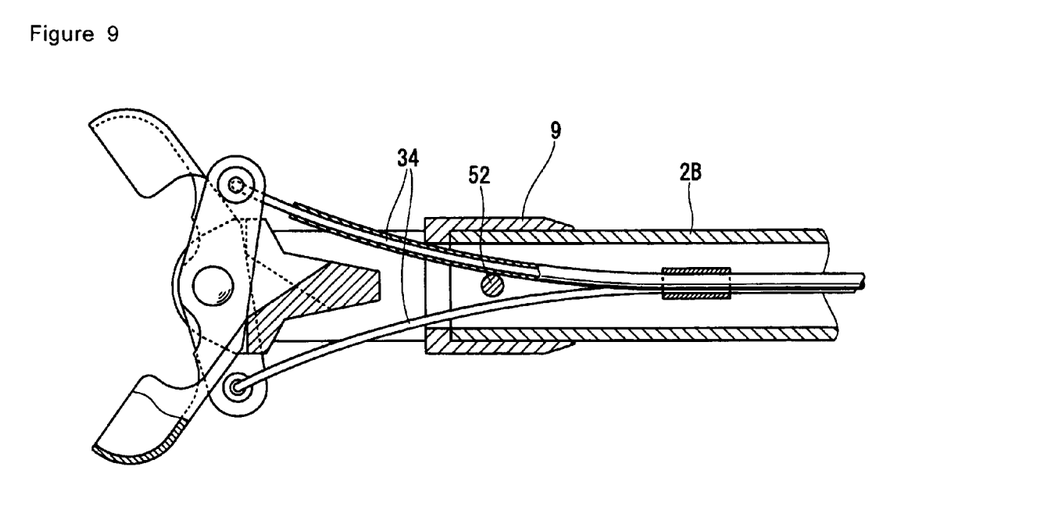
FIG. 9 is a longitudinal cross sectional view of the bipolar high frequency treatment device shown in FIG. 8.

FIG. 8 is a horizontal cross sectional view showing the main parts of a bipolar high frequency treatment device according to the third embodiment of the present invention, and FIG. 9 is a longitudinal cross sectional view of the bipolar high frequency treatment device shown in FIG. 8.

A bipolar high frequency treatment device 1B according to the third embodiment comprises a catheter tube 2B with one through hole running from the top end to the rear end; and an insulating separation member, for example, a through pin 52 disposed in the vicinity of the top end of the catheter tube 2B so as to penetrate the support member 5 and the catheter tube 2B in the direction of the diameter of the catheter tube 2B which is inserted into the support member 5.

In this bipolar high frequency treatment device 1B, since the wires 34 and 34 are separated in two directions at the exit of the catheter tube 2B by the through pin 52, no entanglement of the wires occurs, and the occurrence of the leakage or the electrical short-circuit due to the electrical contact can be prevented when the first forceps blade 6 and the second forceps blade 7 are opened or closed. Furthermore, the through pin 52 ensures the fixing between the support member 5 and the catheter tube 2B, and the rotation and the deformation at the distal end of the catheter tube 2B can be prevented.

The insulating separation member is not limited to the through pin, and there are various modified examples available, as long as it is possible to divide the take-out direction of the wires 34 and 34 into two directions. For example, the through pin may be replaced with a separation element.

INDUSTRIAL APPLICABILITY

As described above, the bipolar high frequency treatment device according to the present invention is useful, because the configuration enhances the insulating properties between the first forceps blade and the second forceps blade.

What is claimed is:

1. A bipolar high frequency treatment device comprising: a catheter tube insertable into a human body through a treatment device passage of an endoscope; a first forceps blade and a second forceps blade at the distal end of the catheter tube, wherein the first forceps blade and the second forceps blade can be opened and closed by operating from outside a human body; a support member for supporting the first forceps blade and the second forceps blade so that the blades are able to open and close; and a voltage supplier for supplying a high frequency voltage to the first forceps blade and the second forceps blade, wherein the first forceps blade comprises a first grip portion, a first pivot support portion coupled with a first wire transmitting an operating force from outside of a human body, a first supported portion located midway between the first grip portion and the first pivot support portion and pivotably supported by the support member, and the first forceps blade is made of an electrically conductive material;

wherein the second forceps blade comprises a second grip portion, a second pivot support portion coupled with a second wire transmitting an operation force from outside a human body, a second supported portion located midway between the second grip portion and the second pivot support portion and pivotably supported by the support member, and the second forceps blade is made of an electrically conductive material; and wherein the support member is made of an insulating material, and comprises;

a tube receiving portion formed in the shape of a cylinder, into which the distal end of the catheter tube is fitted;

a pair of side portions separated and extended in the direction opposite the receiving space for the catheter tube in the tube receiving portion; and a separation element located between the side portions and having:

a first receiving groove for receiving the first pivot support portion, a second receiving groove for receiving the second pivot support portion a central element with first and second opposite faces for separating the first receiving groove and the second receiving groove, the central element located at a distal end portion, opposite the tube receiving portion, of the support member, and a protruding portion extending toward the tube receiving portion of the support member, a proximal end of the protruding portion located beyond the first and second pivot support portions when the first and second forceps blades are in closed state.

2. The bipolar high frequency treatment device according to claim 1, wherein the first forceps blade has the first supported portion and the first pivot support portion formed in the shape of a continuous plate, and the first supported portion has a first grip portion formed at the end portion thereof, opposite the first pivot support portion, and the second forceps blade has the second supported portion and the second pivot support portion formed in the shape of a continuous plate, and the second supported portion has a second grip portion formed at the end portion thereof, opposite the second pivot support portion.

3. The bipolar high frequency treatment device according to claim 1, wherein the first receiving groove comprises a first opening-degree control portion to control an opening angle between the first forceps blade and the second forceps blade when the first forceps blade and the second forceps blade are opened, and the second receiving groove comprises a second opening-degree control portion to control an opening angle between the first forceps blade and the second forceps blade when the first forceps blade and the second forceps blade are opened.

4. The bipolar high frequency treatment device according to claim 3, wherein the first grip portion comprises a first storing portion with a shape of a concavity and a first connecting portion to connect the first storing portion with the first supported portion, and the width of the first connecting portion is broadened as the first connecting portion runs in the direction from the first supported portion to the first storing portion, and the second grip portion comprises a second storing portion with a shape of a concavity and a second connecting portion to connect the second connecting portion with the second supported portion, and the width of the second storing portion is broadened as the second connecting portion runs in the direction from the second supported portion to the second storing portion, wherein the first storing portion does not contact the second pivot support portion and the second storing portion does not contact the first pivot support portion when the first forceps blade and the second forceps blade are opened.

5. The bipolar high frequency treatment device according to claim 4, wherein the first receiving groove is delimited by:
one of the side portions,
the first face of the central element, and
a first inclined wall formed on the first face of the central element and adjoining the protruding portion; and
the second receiving groove is delimited by:
the other of the side portions,
the second face of the central element, and
a second inclined wall formed on the second face of the central element and adjoining the protruding portion.

6. The bipolar high frequency treatment device according to claim 5, wherein the first receiving groove is further delimited by the first opening-degree control portion wherein the first opening-degree control portion is formed on the first face of the central element, adjoins the first inclined wall and extends away from a longitudinal axis of the support member; and the second receiving groove is further delimited by the second opening-degree control portion wherein the second opening-degree control portion is formed on the second face of the central element, adjoins the second inclined wall and extends away from a longitudinal axis of the support member.

7. The bipolar high frequency treatment device according to claim 3, wherein the first receiving groove is delimited by:
one of the side portions,
the first face of the central element, and
a first inclined wall formed on the first face of the central element and adjoining the protruding portion; and
the second receiving groove is delimited by:
the other of the side portions,
the second face of the central element, and
a second inclined wall formed on the second face of the central element and adjoining the protruding portion.

8. The bipolar high frequency treatment device according to claim 7, wherein the first receiving groove is further delimited by the first opening-degree control portion wherein the first opening-degree control portion is formed on the first face of the central element, adjoins the first inclined wall and extends away from a longitudinal axis of the support member; and the second receiving groove is further delimited by the second opening-degree control portion wherein the second opening-degree control portion is formed on the second face of the central element, adjoins the second inclined wall and extends away from a longitudinal axis of the support member.

9. The bipolar high frequency treatment device according to claim 1, wherein the support member integrally has the tube receiving portion, the side portions, and the separation element.

10. The bipolar high frequency treatment device according to claim 1, each of the opposite surfaces of the first grip portion and the second grip portion is made of ceramic.

11. The bipolar high frequency treatment device according to claim 1, wherein the catheter tube has at least two through holes running from the distal end thereof to the proximal end, and has a notch at the distal end of the catheter tube; and a part of the protruding portion is capable of being inserted into the notch wherein the proximal end of the protruding portion contacts a separating wall between the two through holes and forms two passages, for the first and second wires, one of which communicates with one through hole and the other of which communicates with the other through hole.

12. The bipolar high frequency treatment device according to claim 11, wherein
the first receiving groove is delimited by:
one of the side portions,
the first face of the central element, and
a first inclined wall formed on the first face of the central element and adjoining the protruding portion; and
the second receiving groove is delimited by:
the other of the side portions,
the second face of the central element, and
a second inclined wall formed on the second face of the central element and adjoining the protruding portion.

13. The bipolar high frequency treatment device according to claim 12, wherein the first receiving groove is further delimited by a first opening-degree control portion to control an opening angle between the first forceps blade and the second forceps blade when the first forceps blade and the second forceps blade are opened, wherein the first opening-degree control portion is formed on the first face of the central element, adjoins the first inclined wall and extends away from a longitudinal axis of the support member; and the second receiving groove is further delimited by a second opening-degree control portion to control an opening angle between the first forceps blade and the second forceps blade when the first forceps blade and the second forceps blade are opened, wherein the second opening-degree control portion is formed on the second face of the central element, adjoins the second inclined wall and extends away from a longitudinal axis of the support member.

14. The bipolar high frequency treatment device according to claim 1, wherein the catheter tube has one through hole running from the distal end to the proximal end, and an insulating partitioning member traverses a cross section of the catheter tube along the diameter of the catheter tube with penetrations through the support member and the catheter tube in the vicinity of the distal end of the catheter tube, wherein the first wire runs through one side of the insulating partitioning member and the second wire runs through the other side thereof.

15. The bipolar high frequency treatment device according to claim 14, wherein the first receiving groove is delimited by:
one of the side portions,
the first face of the central element, and
a first inclined wall formed on the first face of the central element and adjoining the protruding portion; and
the second receiving groove is delimited by:
the other of the side portions,
the second face of the central element, and
a second inclined wall formed on the second face of the central element and adjoining the protruding portion.

16. The bipolar high frequency treatment device according to claim 15, wherein the first receiving groove is further delimited by a first opening-degree control portion to control an opening angle between the first forceps blade and the second forceps blade when the first forceps blade and the second forceps blade are opened, wherein the first opening-degree control portion is formed on the first face of the central element, adjoins the first inclined wall and extends away from a longitudinal axis of the support member; and the second receiving groove is further delimited by a second opening-degree control portion to control an opening angle between the first forceps blade and the second forceps blade when the first forceps blade and the second forceps blade are opened, wherein the second opening-degree control portion is formed on the second face of the central element, adjoins the second inclined wall and extends away from a longitudinal axis of the support member.

17. The bipolar high frequency treatment device according to claim 1, wherein the first receiving groove and the second receiving groove extend in the separation element toward the tube receiving portion.

18. The bipolar high frequency treatment device according to claim 17, wherein the first receiving groove is delimited by:
  one of the side portions,
  the first face of the central element, and
  a first inclined wall formed on the first face of the central element and adjoining the protruding portion; and
the second receiving groove is delimited by:
  the other of the side portions,
  the second face of the central element, and
  a second inclined wall formed on the second face of the central element and adjoining the protruding portion.

* * * * *

UNITED STATES PATENT AND TRADEMARK OFFICE
CERTIFICATE OF CORRECTION

PATENT NO.          : 8,562,604 B2                                     Page 1 of 1
APPLICATION NO. : 10/568871
DATED                  : October 22, 2013
INVENTOR(S)         : Miyuki Nishimura It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2159 days.

Signed and Sealed this

Fifteenth Day of September, 2015

Michelle K. Lee
*Director of the United States Patent and Trademark Office*